United States Patent
Blondeau et al.

(10) Patent No.: US 7,526,327 B2
(45) Date of Patent: Apr. 28, 2009

(54) INSTRUMENT HAVING OPTICAL DEVICE MEASURING A PHYSIOLOGICAL QUANTITY AND MEANS FOR TRANSMITTING AND/OR RECEIVING DATA

(75) Inventors: Fabien Blondeau, Chézard-St. Martin (CH); Nakis Karapatis, Premier (CH)

(73) Assignee: ETA SA Manufacture Horlogère Suisse, Grenchen (CH)

(*) Notice: Subject to any disclaimer, the term of this patent is extended or adjusted under 35 U.S.C. 154(b) by 811 days.

(21) Appl. No.: 10/860,774

(22) Filed: Jun. 4, 2004

(65) Prior Publication Data
US 2005/0020927 A1    Jan. 27, 2005

(30) Foreign Application Priority Data
Jun. 4, 2003 (CH) .................................... 0986/03
Jun. 4, 2003 (EP) .................................... 03012707

(51) Int. Cl.
*A61B 5/00* (2006.01)
*A61B 5/02* (2006.01)

(52) U.S. Cl. ............... 600/310; 600/322; 600/323; 600/324; 600/500; 600/504; 600/300

(58) Field of Classification Search ............... 600/324, 600/502, 507
See application file for complete search history.

(56) References Cited

U.S. PATENT DOCUMENTS

| | | | |
|---|---|---|---|
| 4,674,743 A | 6/1987 | Hirano | |
| 5,622,180 A | 4/1997 | Tammi et al. | |
| 5,776,056 A | 7/1998 | Bu | |
| 5,810,736 A | 9/1998 | Pail | |
| 6,002,952 A * | 12/1999 | Diab et al. | 600/310 |
| 2002/0125991 A1* | 9/2002 | Levin | 340/5.8 |
| 2002/0165436 A1 | 11/2002 | Schluter | |
| 2003/0065269 A1 | 4/2003 | Vetter et al. | |

FOREIGN PATENT DOCUMENTS

| | | |
|---|---|---|
| EP | 0 842 635 A1 | 5/1998 |
| EP | 0 940 119 A1 | 9/1999 |
| EP | 1 101 439 A2 | 5/2001 |
| EP | 1 297 784 A1 | 4/2003 |
| JP | 2001-299709 * | 10/2001 |
| WO | WO 99/41647 | 8/1999 |

OTHER PUBLICATIONS

European Search Report, completed Nov. 3, 2003.
Austrian Search Report in corresponding Signapore Patent Application No. 200403035-9, completed Mar. 31, 2005.

* cited by examiner

*Primary Examiner*—Patricia C Mallari
(74) *Attorney, Agent, or Firm*—Griffin & Szipl, P.C.

(57) ABSTRACT

There is disclosed a portable instrument including an optical device (4; 5; 6) for measuring a physiological quantity, particularly the heart rhythm, and data emission and/or reception means, the optical device including at least one light source (41; 51; 61) for subjecting a portion of an organic tissue (10) to a light emission and at least one photoreceptor (42; 52, 53, 54; 62, 64, 66) for detecting the intensity of the light emission after propagation in the organic tissue. The optical device also forms the data emission and/or reception means, said at least one light source and/or said at least one photoreceptor being arranged for respectively emitting data to an external unit or receiving data from said external unit.

7 Claims, 3 Drawing Sheets

INSTRUMENT HAVING OPTICAL DEVICE MEASURING A PHYSIOLOGICAL QUANTITY AND MEANS FOR TRANSMITTING AND/OR RECEIVING DATA

This application claims priority from European Patent Application No. 03012707.0, filed Jun. 4, 2003 and Swiss Patent Application No. 0986/03, filed Jun. 4, 2003. The entire disclosures of the above patent applications are hereby incorporated by reference.

FIELD OF THE INVENTION

The present invention concerns generally a portable instrument including an optical device for measuring a physiological quantity, particularly the heart rhythm, and means for the emission and/or reception of data, this optical device including at least one light source for subjecting a portion of an organic tissue to a light emission and at least one photoreceptor for detecting the intensity of the light emission after propagation in the organic tissue.

BACKGROUND OF THE INVENTION

Such portable measuring instruments are already known. These portable devices are particularly employed for detecting, by optical means, the heart rhythm and/or the level of oxygen in a patient's blood. They are found in various forms ranging from clamps intended to be placed on a zone of the human body (typically on the end of a finger, on the earlobe or any other extremity of the human body sufficiently irrigated by blood) to devices worn on the wrist having a similar appearance to a wristwatch.

Within the scope of an application to measurement of the heart rhythm, the optical device is used for generating adequate illumination of a portion of the organic tissue (typically the skin) and includes one or several photoreceptors for detecting the intensity of the light emission produced by the optical device after propagation in the organic tissue. Variations in the blood flow pulsation induce a variation in the absorption of the luminous emission produced by the optical device, the frequency of said absorption variation essentially corresponding to the frequency of the heart pulsations. Detection of the intensity of the light emission after propagation in the organic tissue accompanied by adequate processing of the measurement signal or signals enables one to extract an indication of the heart rhythm. The optical devices commonly used for this type of application are relatively simple and typically consist of LEDs (light emitting diodes) emitting within a determined wavelength range, associated with one or several photoreceptors, typically photodiodes.

In addition to the function of measuring the desired physiological quantity, the portable instruments fitted with optical devices of the aforementioned types are also commonly fitted with means for emitting and/or receiving data. In particular, emission means are typically provided for downloading onto an external terminal data measured and stored in the portable instrument during periods of activity, for example during physical activity or during a health diagnosis. Moreover, reception means can be provided for loading configuration data in the portable instrument, for example limit values for the measured physiological quantity such as minimum and maximum heart rhythm values, between which the user wishes to keep his heart rhythm. The data emitted from the portable instrument or received by the portable instrument may or may not be related to the measured physiological quantity.

The emission and/or the reception of data can commonly be carried out by direct cable link or preferably owing to wireless communication means that may, for example, be of the acoustic, optical, inductive or radio-frequency type.

Patent document Nos. U.S. Pat. No. 4,674,743, EP 0 842 635 and U.S. Pat. No. 5,776,056 disclose various portable instruments provided with an optical device of the aforementioned type for measuring a physiological quantity as well as optical data communication means. These documents however disclose solutions employing distinct optical devices.

As mentioned, other known solutions rely upon communication means of the acoustic, inductive or radio-frequency type. By way of example, documents EP 0 940 119, U.S. Pat. No. 5,810,736, U.S. Pat. No. 5,622,180 or WO 99/41647 and EP 1 101 439 can be cited.

All of the aforementioned prior art solutions, including solutions employing optical communication means, have the drawback of requiring specific additional requirements which influence the manufacturing costs of the portable instrument and inevitably require space in order to be incorporated. These solutions are not, therefore, optimal in terms of compactness and manufacturing costs.

It is thus a general object of the present invention to propose a portable instrument of the aforementioned type, which allows both a reduction in costs and a reduction in the size of the portable instrument with respect to solutions of the prior art.

SUMMARY OF THE INVENTION

The present invention thus concerns a portable instrument whose features are set out in claim 1.

Advantageous embodiments of the present invention form the subject of the dependent claims.

According to the solution proposed, the invention thus proposes to use the optical device normally employed as means for measuring the physiological quantity as emission means and/or data reception means. More particularly, at least one light source of the optical device is used for emitting data to an external unit, and/or at least one photoreceptor of the optical device is used for receiving data transmitted from the external unit.

During operation, the optical device is advantageously switched between a measuring phase during which it operates as means for measuring the physiological quantity and a communication phase during which it operates as data emission and/or reception means, the portable instrument further including memory means for storing, during the measuring phase, data relating to the change over time of said physiological quantity prior to transmission, during the communication phase, to the external unit.

According to particular embodiments, means are also proposed for automatically activating the measuring function or the data emission/reception function of the optical device.

The proposed solution thus has the advantage of an optimal use of the components already present in the portable instrument thus reducing the manufacturing costs and favouring better use of the space available in the instrument.

BRIEF DESCRIPTION OF THE DRAWINGS

Other features and advantages of the present invention will appear more clearly upon reading the following detailed description of various embodiments of the invention given solely by way of non-limiting example and illustrated by the annexed drawings, in which.

DESCRIPTION OF PREFERRED EMBODIMENTS

The various embodiments that will now be presented are given solely by way of non-limiting illustration. In particular, it should be stressed that the embodiments that will be presented can advantageously, but not solely, be implemented in an instrument for wear on the wrist. Other portable applications can perfectly well be envisaged.

Figure 1:
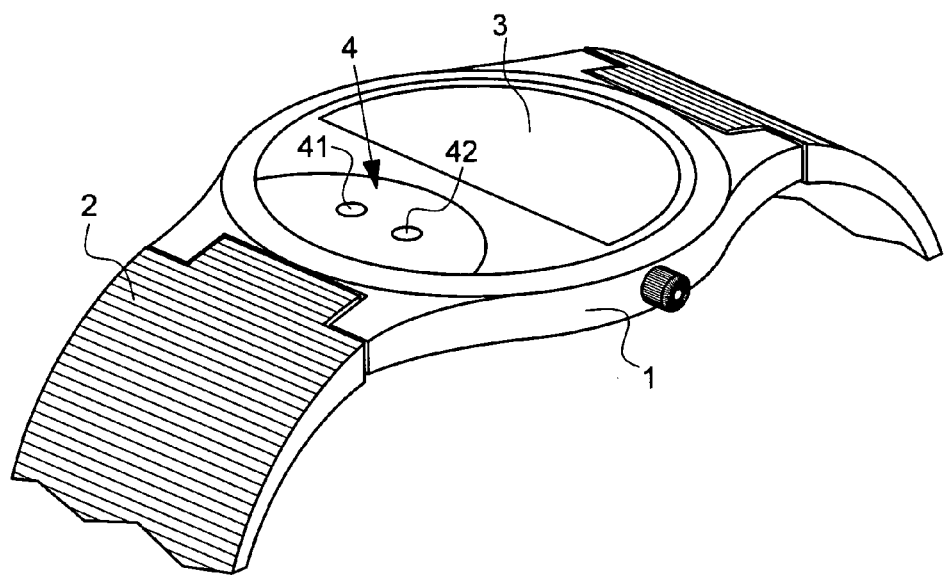
FIG. 1 shows a perspective view on the display side of a portable instrument for measuring a physiological quantity according to a first embodiment example taking a similar form to that of a wristwatch and including an optical device arranged on the front face of the instrument.
Figure 2:
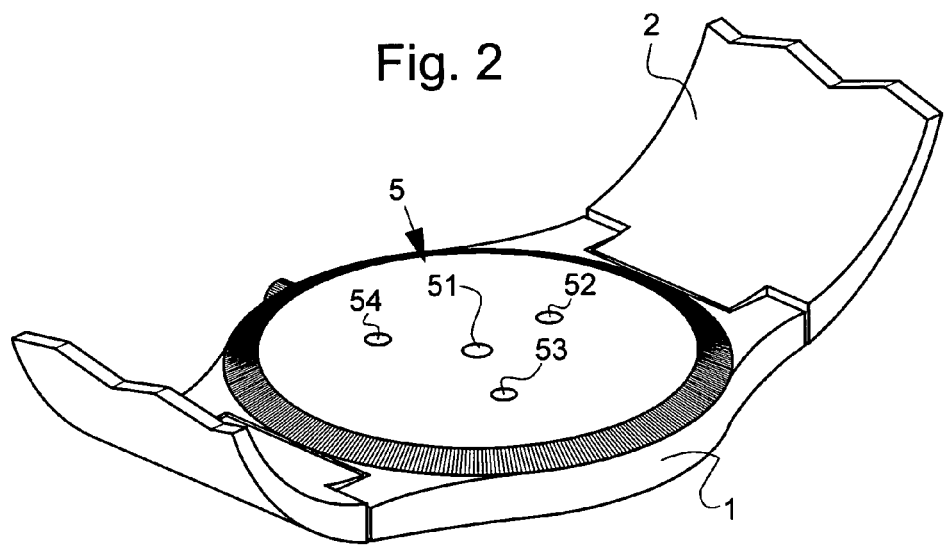
FIG. 2 shows a perspective view on the bottom side of the portable instrument for measuring a physiological quantity according to a second embodiment example also taking a similar form to that of a wristwatch and including an optical device arranged in the bottom of the instrument.

FIGS. 1 and 2 show purely by way of non-limiting illustration two embodiment examples of a portable instrument for measuring a physiological quantity which both take a similar form to that of a wristwatch. Both thus include a case 1 forming a middle part in this example and a wristband 2 attached in a conventional manner to case 1. A display device 3 is also disposed on the front face of the instrument, this display device 3 only appearing in the example of FIG. 1. The difference between the two examples of FIGS. 1 and 2 essentially lies in the positioning and configuration of the optical device (designated as a whole by the reference numeral 4, respectively, 5) employed for measuring the desired physiological quantity (for example the heart rhythm or the level of oxygen in the blood as already mentioned).

In the example of FIG. 1, optical device 4 is placed on the front face of the portable instrument in proximity to display device 3. Optical device 4 includes here a single light source 41 cooperating with a single photoreceptor 42. As already mentioned, light source 41 is typically a light emitting diode (LED) emitting within a determined wavelength range (for example infrared or any other suitable wavelength range) and photoreceptor 42 can be a photodiode, a phototransistor or any other suitable optical receiver having a response adapted to the wavelength range of light source 41.

According to the example of FIG. 1, it will be understood that the desired physiological quantity measurement is for example carried out by placing a finger on the front face of the portable instrument opposite optical device 4.

In the example of FIG. 2, the optical device, designated 5, is placed in the bottom of the instrument. Unlike the example of FIG. 1, optical device includes, in addition to a light source 51 essentially placed in a central region of the bottom of the portable instrument, three photoreceptors 52, 53 and 54 placed symmetrically around central light source 51. The use of several photoreceptors arranged around one or several light sources is generally preferred to the solution of FIG. 1, essentially for the purpose of ensuring better measurement reliability. On this last point, in order to obtain more ample information on an optical system for measuring the heart rhythm, employing at least two detection channels, reference can be made to the document EP 1 297 784, which shows an embodiment example of a similar portable instrument to that of FIG. 2.

Figure 3:
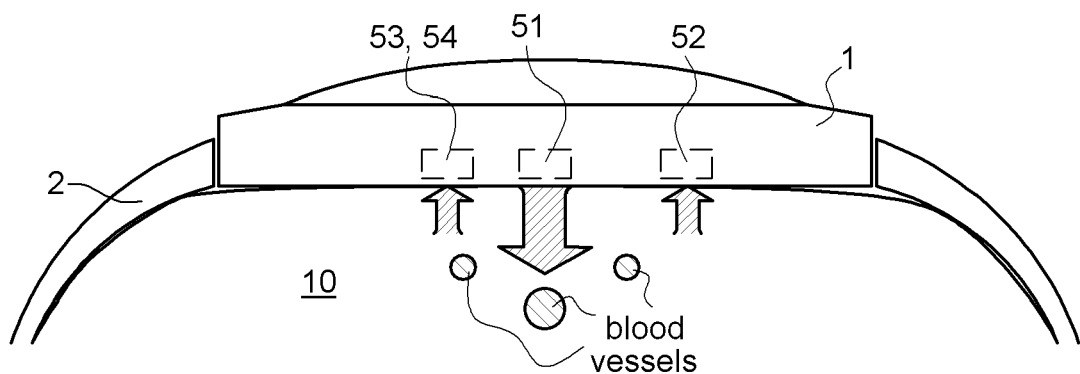
FIG. 3 is a cross-section of the instrument of FIG. 2 taken along the longitudinal direction of the wristband when the instrument is being worn on the wrist for taking the measurement of the physiological quantity.

FIG. 3 is a cross-section of the portable instrument of FIG. 2 taken in the longitudinal direction of the wristband when the latter is worn on the wrist (designated by the general reference numeral 10 in the Figure). Unlike the example of FIG. 1, the portable instrument and its optical device 5 is permanently brought into contact here with the user's organic tissue when the instrument is worn. The light emission produced by source 51 is arranged for penetrating the organic tissue sufficiently deeply to be modulated by the blood flow irrigating the illuminated organic tissue. The modulated light emission is detected after reflection by photoreceptors 52 to 54 of the optical device.

Figure 4:
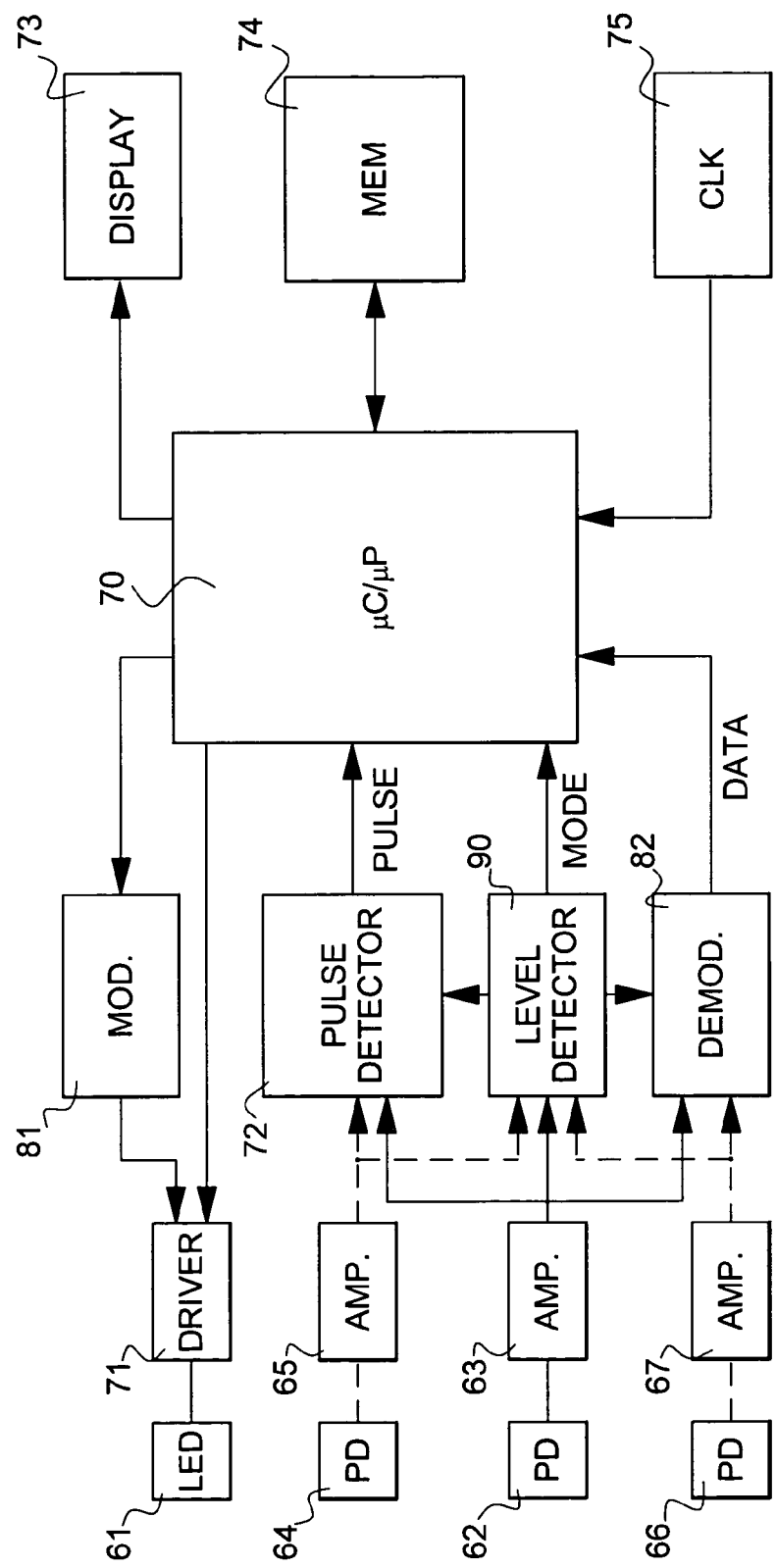
FIG. 4 is a block diagram illustrating various components of the portable instrument according to an embodiment example.

FIG. 4 shows a block diagram illustrating the main constituent components of the portable instrument in accordance with one embodiment of the invention. As illustrated, the portable instrument includes a light source 61 (for example a light emitting diode (LED) or any other suitable device) coupled to a control circuit 71 the operation of which is controlled by a central processing unit 70, such as a microprocessor or microcontroller. This central unit 70 is also interfaced with a display device 73 (of the analogue and/or digital type), memory means 74 (RAM, ROM, EEPROM, FLASH or suchlike) and a clock system 75 assuring adequate clocking of operation of central unit 70 and its peripheral components. This clock system 75 can also fulfil the conventional clock functions of a timekeeper.

Central processing unit 70 is also coupled to a circuit 72 dedicated to the detection and measurement of the desired physiological quantity (particularly the heart rhythm), the functions of this circuit being however able to be integrated with those of the central processing unit. The functions of this circuit have already been briefly touched upon and are essentially aimed at extracting information relating to the physiological quantity from the optical signals detected by the associated photoreceptor or photoreceptors. In the present case, a first photoreceptor 62 is coupled to the detection circuit 72 via amplification means and, if necessary, filtering means 63. Information relating to the desired physiological quantity is transmitted to central unit 72, particularly for the purpose of being displayed on device 73 and/or, preferably, stored in memory means 74 for subsequent consultation.

One will not enlarge upon the method for measuring the physiological quantity here since this question does not directly concern the subject of the present invention. Moreover, various solutions exist for carrying out this measurement. One particularly effective solution for measuring the heart rhythm is described in ample detail in the aforementioned document EP 1 297 784, which is incorporated here by reference.

In the embodiment example of FIG. 4, in order to be able to transmit and/or receive data by means of its optical device, the portable instrument further includes, on the one hand, modulation means 81, coupled between control circuit 71 of the light source and central unit 70, and, on the other hand, demodulation means 82, coupled between amplification means 63 associated with photoreceptor 62 and central unit 70.

It will be understood that the purpose of modulation means 81 is to control control circuit 71 so as to produce a modulated optical signal by means of the associated light source 61. Likewise, it will be understood that the purpose of demodulation means 82 is, conversely, to decode a modulated light signal picked up by the associated photoreceptor 62. Any type of modulation can be used for the data transmission and reception. It may be conventional amplitude, phase, frequency or code modulation. Moreover, distinct modulations could be adopted for transmitting and receiving the data so as to clearly identify whether it is an ingoing or outgoing emission. In any case, the optical signals are modulated on the basis of the data to be transmitted.

In FIG. 4, it will be noted that the portable instrument can include more than one light source and/or more than one photoreceptor. In particular, as represented by the dotted lines in FIG. 4, a second photoreceptor 64 and associated amplification means 65 could be coupled to detector 72, the latter not necessarily being coupled to demodulation means 82. Likewise, a third photoreceptor 66 and associated amplification means 67 could be coupled to demodulation means 82 without however being coupled to detector 72. This third photoreceptor would not then participate in detection of the desired physiological quantity, but only in data reception.

Generally, within the scope of the present invention, it should be noted that it would suffice if at least one light source or one photoreceptor of the optical device, normally used for the measurement of the desired physiological quantity, were also used respectively for transmitting or receiving data. Indeed, one can already hope to obtain an advantage in terms of reducing manufacturing costs and simplifying construction by using only one light source or photoreceptor for fulfilling both functions. It should also be noted that it could be preferable to use a specific photoreceptor dedicated solely to measuring the physiological quantity and an additional photoreceptor for receiving data, this being justified by constraints in terms of sensitivity.

Within the scope of the present invention, it will also be advantageous to provide the instrument with detection means for automatically and selectively activating the physiological quantity measuring function or the data emission/reception function of the optical device.

By way of first example, the portable instrument could thus include first detection means for automatically activating the physiological quantity measuring function of the optical device when the latter is brought into contact with organic tissue. One advantageous solution could consist in determining whether the optical device is in contact with organic tissue on the basis of the intensity of the light emission detected by at least one photoreceptor.

By way of second example, the portable instrument could also include second detection means for automatically activating the data emission and/or reception function of the optical device when data is emitted for the portable instrument. One advantageous solution could also consist in detecting whether data has been emitted for the portable instrument on the basis of the intensity of the light emission detected by at least one photoreceptor.

With reference once again to FIG. 4, it is thus advantageous also to provide the portable instrument with means 90 for detecting the level of intensity of the light emission picked up by one or several photoreceptors. It would, in practice, be possible to envisage differentiating an optical signal transmitted by an external unit from an optical signal or signals typically picked up by the same photoreceptors when the portable instrument is operating in measuring mode, the intensity of the optical signal produced by an external unit being able to be adjusted to have a higher intensity level than the mean level of the optical signals during a physiological quantity measurement.

Figure 5:
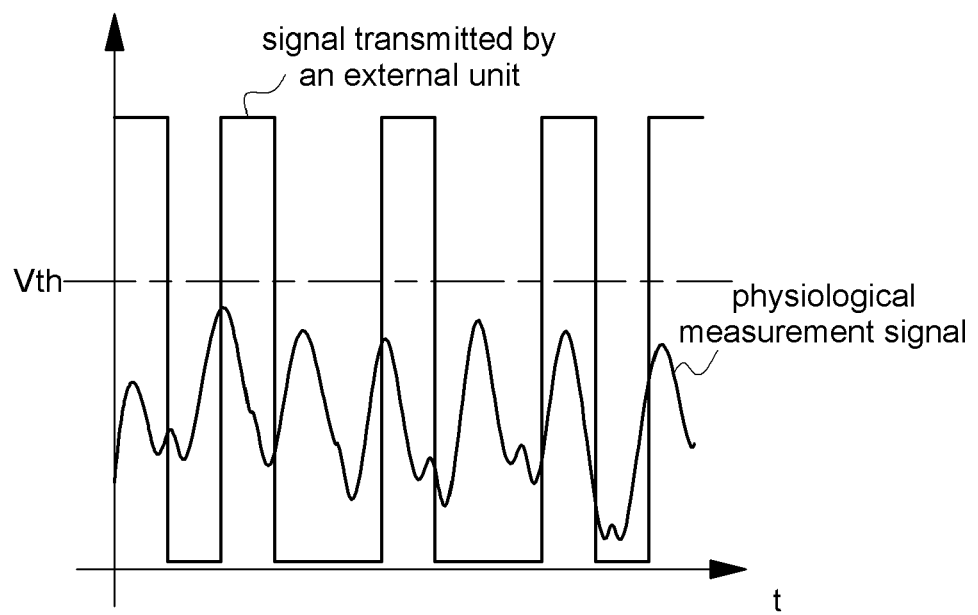
FIG. 5 is a diagram illustrating schematically how to envisage differentiating the optical signals transmitted by an external unit from the optical signals picked up during measurement of the physiological quantity, for the purpose of selectively activating the appropriate operating mode of the portable instrument.

FIG. 5 schematically illustrates this possibility by an evolution over time diagram in which there are added by way of example a line representative of an optical heart rhythm measurement and a line representative of a modulated signal transmitted by an external unit, the respective intensity of these signals being selected to be substantially different. By imposing a detection threshold Vth as illustrated, the two types of signals could thus be differentiated and the portable instrument switched into the appropriated mode.

Starting from this principle, selective activation of detector 72 or demodulator 82 could be carried out by means 90. Demodulator 82 could also be used for decoding and detecting the presence of a predetermined optical control signal transmitted by the external unit. Thus, a first optical control signal encoded in accordance with a known sequence of the portable instrument could be transmitted by the external unit to warn the portable instrument that data (for example configuration data) will be transmitted thereto. Likewise, a second optical control signal encoded in accordance with another known code sequence of the portable instrument could be transmitted to the external unit to require the portable instrument to emit data (for example data relating to the evolution over time of the measured physiological quantity stored in memory means 74).

If differentiation between the optical signals based on the intensity of the signals picked up alone is not sufficient, means 90 could alternatively be arranged for differentiating the signals on the basis of distinctive modulation features of the optical signal transmitted by the external unit, for example on the basis of a frequency analysis of the received signals. It will be understood that other equivalent means may also be envisaged.

It will be understood finally that various modifications and/or improvements evident to those skilled in the art can be made to the embodiments described in the present description without departing from the scope of the invention defined by the annexed claims. In particular, the present invention is not limited solely to use in a wristwatch but also applies to any other portable application, whether worn on the wrist or not.

What is claimed is:

1. A portable instrument including an optical device capable of measuring a physiological quantity, for example the heart rhythm, and emitting and/or receiving data, said optical device including at least one light source for subjecting a portion of an organic tissue to a light emission and at least one photoreceptor for detecting the intensity of the light emission after propagation in said organic tissue, wherein said optical device also emits and/or receives data, said at least one light source and/or said at least one photoreceptor being arranged for respectively emitting data to an external unit or receiving data from said external unit, and wherein said optical device has a measuring phase during which it operates as means for measuring said physiological quantity and a communication phase during which it operates as data emission and/or reception means and is operable to be switched between the measuring and communication phases, the portable instrument further including memory means for storing data, during said measuring phase, relating to the evolution over time of said physiological quantity prior to transmission of said data, during said communication phase, to said external unit.

2. The portable instrument according to claim 1, wherein said optical device is arranged such that, when said portable instrument is being worn, it is brought into permanent contact with the organic tissue in order to operate as means for measuring said physiological quantity, said optical device being arranged to operate as data emission and/or reception means when said portable instrument is not being worn.

3. A portable instrument including an optical device capable of measuring a physiological quantity, for example the heart rhythm, and emitting and/or receiving data, said optical device including at least one light source for subjecting a portion of an organic tissue to a light emission, at least one photoreceptor for detecting the intensity of the light emission after propagation in said organic tissue, wherein said optical device also emits and/or receives data, said at least one light source and/or said at least one photoreceptor being arranged for respectively emitting data to an external unit or receiving data from said external unit, further comprising first detection means for automatically activating the physiological quantity measuring function of said optical device when the first detection means is brought into contact with the organic tissue.

4. The portable instrument according to claim 3, wherein said first detection means determines whether said optical device is in contact with the organic tissue on the basis of the intensity of the light emission detected by at least one photoreceptor of the optical device.

5. The portable instrument according to claim 3, further comprising second detection means for automatically detecting the data emission and/or reception function of said optical device when data is emitted to said portable instrument.

6. The portable instrument according to claim 5, wherein said second detection means detects whether data is emitted to the portable instrument on the basis of the intensity of the light emission detected by at least one photoreceptor of the optical device.

7. The portable instrument according to claim 5, wherein the data emission function and the data reception function of said optical device are selected on the basis of predetermined optical control signals transmitted by the external unit.

* * * * *